United States Patent [19]

Bass

[11] 4,117,149

[45] Sep. 26, 1978

[54] 4-OXO-4H-BENZOPYRANS AS ANIMAL GROWTH PROMOTANTS

[75] Inventor: Robert John Bass, Birchington, England

[73] Assignee: Pfizer Inc., New York, N.Y.

[21] Appl. No.: 795,652

[22] Filed: May 10, 1977

Related U.S. Application Data

[62] Division of Ser. No. 714,086, Aug. 13, 1976, abandoned.

[30] Foreign Application Priority Data

Sep. 12, 1975 [GB] United Kingdom .............. 37553/75

[51] Int. Cl.$^2$ ..................... A61K 31/35; C07D 311/02
[52] U.S. Cl. .................................. 424/283; 260/345.2
[58] Field of Search ....................... 424/283; 260/345.2

[56] References Cited

U.S. PATENT DOCUMENTS

| 3,833,730 | 9/1974 | Feuer et al. ........................ 424/283 |
| 3,907,830 | 9/1975 | Feuer et al. ........................ 424/283 |

*Primary Examiner*—V. D. Turner
*Attorney, Agent, or Firm*—Connolly and Hutz

[57] ABSTRACT

4-Oxo-4H-benzopyrans are described which are capable of promoting growth or improving feed conversion efficiency in economically important animals.

1 Claim, No Drawings

4-OXO-4H-BENZOPYRANS AS ANIMAL GROWTH PROMOTANTS

CROSS REFERENCE TO RELATED APPLICATION

This application is a division of application Ser. No. 714,086, filed Aug. 13, 1976, now abandoned.

BACKGROUND OF THE INVENTION

Many 3-substituted-4-oxo-4H-benzopyrans are known and various 3-phenyl derivatives (isoflavones) have been proposed for use as feed additives for promoting the growth or improving feed conversion efficiency in econically important animals. Other 3-substituted-4-oxo-4H-benzopyrans have been proposed as anti-allergic drugs.

Existing processes for the preparation of such compounds are frequently multistage and of limited utility, as for example, the synthesis of isoflavones described by Baker and Ollis, Nature 169, 706 (1952) and by Baker, Chadderton Harborne and Ollis, J. Chem. Soc., 1852 (1953). The use of the Vilsmeier reaction has been described by Kagal, Nair and Venkataraman, Tetrahedron Letters 593 (1962) but this process is not of general utility. For example, it fails in the case of polyhydroxyphenyl ketones. In addition, when isoflavones are prepared by this process, the major product is commonly a compound in which the aromatic ring is formylated.

SUMMARY OF THE INVENTION

This invention is concerned with a process for the preparation of compounds of the formula

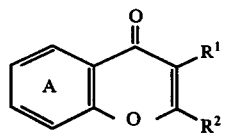

(I)

wherein
R$^1$ represents an aryl group, a heteroaryl group, a cycloalkyl group, an aralkyl group, a lower akoxy group, an aryloxy group, or an aryl-sulphonyl group;
R$^2$ represents a hydrogen atom or a lower alkyl group; and the ring A may optionally be substituted with one or more halogen atoms or hydroxyl, lower alkyl or lower alkoxy groups;
which comprises reacting a 2-hydroxy-phenyl ketone of the formula:

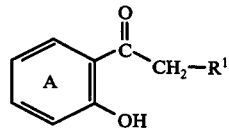

(II)

(wherein R$^1$ and the ring A are as previously defined) with an N,N-dialkyl or N-alkyl-N-aryl-amide of a lower aliphatic acid and a strong acid chloride, in excess reagent or in a reaction inert organic solvent, in the presence of boron-trifluoride etherate.

DETAILED DESCRIPTION OF THE INVENTION

The present invention is concerned with a general process for the preparation of 3-substituted-4-oxo-4H-benzopyrans from 2-hydroxy-phenyl ketones in which the use of a formylating reagent of the Vilsmeier type in the presence of boron trifluoride etherate enables the preparation of such compounds in a single stage without the formation of ring formylated by-product.

A 2-hydroxy-phenyl ketone is contacted with an N,N-dialkyl or N-alkyl-N-aryl-amide of a lower aliphatic acid and an acid chloride, in excess reagent or in a reaction-inert organic solvent, in the presence of boron trifluoride etherate. In the reaction, acylation of the activated methylene group is accompanied by concomitant ring closure to yield, after suitable work-up, the benzopyran compounds of formula I.

The strong acid chloride may be, for example, phosphorus oxychloride, thionyl chloride, phosgene, oxaloyl chloride, methane-sulphonyl chloride, benzene-sulphonyl chloride or para-toluene-sulphonyl chloride. Particularly preferred reagents for effecting the cyclisation are N,N-dimethylformamide or N,N-dimethylacetamide with methane-sulphonyl chloride in the presence of boron-trifluoride etherate. The reaction is preferably carried out with the 2-hydroxyphenyl ketone dissolved in a solvent consisting of excess dry dimethylformamide or dimethylacetamide, and to this solution may be added the boron-trifluoride etherate, preferably in an amount of from 3 to 6 equivalents, based on amount of ketone used. A solution containing methane-sulphonyl chloride dissolved in excess dry dimethylformamide or dimethyl-acetamide is then added, preferably in excess and allowing 1 equivalent excess of methane-sulphonyl chloride for each hydroxyl group present in the ketone used, and the mixture is then heated until the reaction is complete. We have found that when the reaction is performed at 80° C e.g., by heating on a steam bath, the reaction is substantially complete within 2 hours. The product is then conveniently isolated from the reaction mixture by adding water to the cooled reaction mixture or by pouring into a large volume of cold water. The solid product is recovered by filtration and further purification, if required, can be effected by recrystallisation. In the case where dimethylacetamide is used as the solvent to give the 2-methyl compounds of formula (I) where R$^2$=CH$_3$, the product is initially isolated with any hydroxy groups present as substituents in ring A acetylated. The free hydroxy groups may be readily regenerated by mild acid hydrolysis.

We have found the present process to be particularly advantageous for the synthesis of 5,7-dihydroxy-isoflavones of the formula:

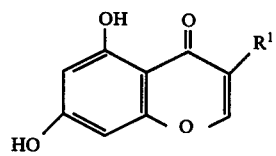

(III)

where R$^1$ is a phenyl or substituted phenyl grup, and for the synthesis of novel 3-substituted 4-oxo-4H-benzopyrans of formula (I) where R$^2$ is hydrogen and R$^1$ is as previously defined other than a phenyl, substituted phenyl or heteroaryl group.

The starting materials of formula (II) are generally known compounds or are readily accessible by conventional methods. For example, they may be obtained by the Houben-Hoesch reaction of a hydroxy-phenol with a nitrile of the formula $R^1CH_2CN$ or by a Friedel-Crafts reaction between a phenol and an acid of the formula $R^1CH_2COOH$ or an ester, acid chloride or anhydride thereof.

The present invention also provides certain novel 5,7-dihydroxy-isoflavones of formula (III) above wherein $R^1$ is a 4-isopropyl-phenyl, 4-bromo-phenyl, p-tolyl, 3-chloro-phenyl, p-biphenyl or 4-methanesulphonyloxy-phenyl group.

Also are provided novel 3-substituted-4-oxo-4H-benzopyrans of formula (I) in which $R^2$ is a hydrogen atom and $R^1$ is as previously defined other than a phenyl, substituted phenyl or heteroaryl group including the following:

5,7-dihydroxy-3-benzyl-4-oxo-4H-benzopyran,
5,7-dihydroxy-3-phenylsulphonyl-4-oxo-4H-benzopyran,
5,7-dihydroxy-3-(4-methoxyphenoxy)-4-oxo-4H-benzopyran,
5,7-dihydroxy-3-methoxy-4-oxo-4H-benzopyran,
7-hydroxy-3-(naphth-1-yl)-4-oxo-4H-benzopyran,
7-hydroxy-3-(naphth-2-yl)-4-oxo-4H-benzopyran,
5-hydroxy-3-(4-hydroxy-benzyl)-7-methyl-4-oxo-4H-benzopyran and compounds in which $R^1$ is a cycloalkyl group containing 5 or 6 carbon atoms, e.g.:

6-hydroxy-3-cyclohexyl-4-oxo-4H-benzopyran,
7-hydroxy-3-cyclopentyl-4-oxo-4H-benzopyran,
6-hydroxy-3-cyclopentyl-4-oxo-4H-benzopyran, and
6-chloro-7-hydroxy-3-cyclohexyl-4-oxo-4H-benzopyran.

The novel compounds of the invention are useful for promoting growth or improving feed conversion efficiency in animals. One particularly preferred novel compound of the invention is 7-hydroxy-3-(naphth-2-yl)-4-oxo-4H-benzopyran. The compound of formula (I) may be administered in the animal feed or drink, or it may be administered to the animal orally in other ways, or parenterally or as an implant. When it is administered in the feed it may be added thereto in amounts of from 1 g to 100 g per tonne of feed. For convenience of distribution it will, however, normally be marketed in the form of a concentrate in which the compound is mixed with an inert diluent such as limestone or oystershell powder or with other feed components, e.g. at levels of from 1 to 100 g per kg of concentrate.

Thus also according to the invention there are provided novel feed compositions for animals which comprise a nutritionally balanced feed composition in which is incorporated a growth promoting or feed conversion efficiency improving amount of a novel compound of the formula (I).

Also according to the invention, a composition suitable for adding to animal feeds comprises a novel compound of the formula (I) together with a solid diluent compatible with animal feeds.

For oral or parenteral administration, or for administration as an implant, the compound of formula (I) may be used as such, but will more generally be used in admixture with a pharmaceutical carrier selected with regard to the intended mode of administration and according to veterinary pharmaceutical practice. For example, it may be administered orally as a bolus or capsule containing excipients such as starch or lactose, or as a drench consisting of a solution or suspension of the compound in an aqueous vehicle containing flavouring matter if necessary. For parenteral administration, e.g. by depot injection, it may be administered as a suspension in a pharmaceutically-acceptable oil, e.g. arachis oil, suitable dosages being in the range from 0.1 to 100 mg per animal. For administration as an implant, it may be formulated as a pellet with an excipient such as maize starch, lactose or glycine to release the active ingredient at an appropriate rate. Such pellets for implants may suitably contain from 50 to 80% of the active ingredient by weight.

The invention will now be more particularly described by reference to the following Examples which illustrate the novel process of the invention and describe the preparation of the novel compounds of formula I.

In the above and elsewhere in this specification the term lower applied to an alkyl or an alkoxy group indicates that such a group contains up to 4 carbon atoms and may be straight or branched chain. Halogen means fluorine, chlorine, bromine or iodine. By "aryl" is meant an aromatic hydrocarbon group, e.g. a phenyl or naphthyl group, which may or may not be substituted; by "heteroaryl" is meant an aromatic heterocyclic group, e.g. a pyridyl group; by "aralkyl" is meant an aryl-substituted lower alkyl group.

EXAMPLE 1

2,4,6-Trihydroxy-phenyl 4-methyl-benzyl-ketone (13.0 g) was dissolved in dry dimethylformamide (100 ml) and boron-trifluoride etherate (42.4 g) was added cautiously, with stirring. A solution of methane-sulphonyl chloride (17.3 g) dissolved in dry dimethylformamide (100 ml) was added and the mixture was heated for 2 hours on the steam bath. The reaction mixture was cooled, poured slowly into cold water (1 l) with stirring and allowed to stand overnight. The solid product was collected by filtration and recrystallised from a mixture of ethanol and water to yield 5,7-dihydroxy-3-p-tolyl-4-oxo-4H-benzopyran (11.5 g, 85% yield), m.p. 215°–217° C. (Found: C, 71.3; H, 4.6. $C_{16}H_{12}O_4$ requires C, 71.6; H, 4.5%)

EXAMPLE 2

The following 3-substituted-5,7-dihydroxy-4-oxo-4H-benzopyrans were prepared starting from the appropriate 2,4,6-trihydroxy-phenyl ketone by the same procedure as described in Example 1. Table I shows the 3-substituent ($R^1$) together with the melting point and analytical data for the compounds. In all cases the compounds were shown to be single component by TLC and the structures were confirmed by NMR and IR spectroscopy.

TABLE I
5,7-Dihydroxy-4-oxo-4H-benzopyrans (formula III)
| Example | R[1] | m.p. °C | Analysis % (Theoretical in brackets) |
|---|---|---|---|
| 2 | 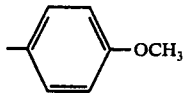 | 211–213° (lit.[1] 211–212°) | |
| 3 | 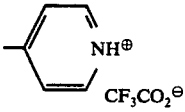 | >330° | C, 52.0; H, 2.7; N, 3.9 (C, 52.0; H, 2.7; N, 3.8)[6] |
| 4 | 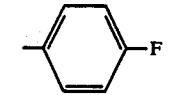 | 225–226° (lit.[2] 224–225°) | |
| 5 | 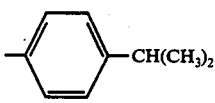 | 136–137° | C, 72.7; H, 5.4 (C, 73.0; H, 5.4) |
| 6 | 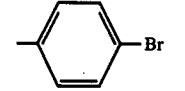 | 250–252° | C, 53.7; H, 2.8 (C, 54.1; H, 2.7) |
| 7 | 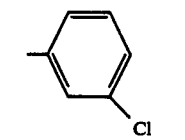 | 230° | C, 62.25; H, 3.1 (C, 62.4; H, 3.1) |
| 8 | 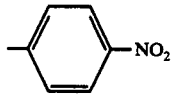 | 301–303° (lit.[3] 294–295°) | C, 59.5; H, 3.00; N, 5.1 (C, 59.3; H, 3.1; N, 4.6)[4] |
| 9 | 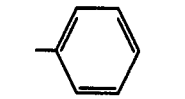 | 195–196° (lit.[3] 206–208°) | |
| 10 | 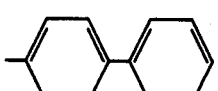 | 245–247° | C, 74.7; H, 4.4 (C, 74.3; H, 4.45)[4] |
| 11 | 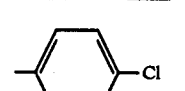 | 236° (lit.[2] 236–237°) | |
| 12 | 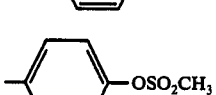 | 178° | C, 52.6; H, 3.55 (C, 52.2; H, 3.7)[5] |
| 13 | 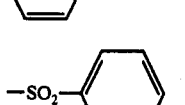 | 233–235° | C, 56.5; H, 3.4 (C, 56.6; H, 3.2) |
| 14 | 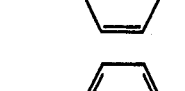 | 177–178° | C, 70.7; H, 4.5 (C, 70.5; H, 4.6)[4] |
| 15 | —OCH$_3$ | 229–231° | C, 57.2; H, 3.8 (C, 57.7; H, 3.9) |

TABLE I-continued

5,7-Dihydroxy-4-oxo-4H-benzopyrans (formula III)

| Example | R[1] | m.p. °C | Analysis % (Theoretical in brackets) |
|---|---|---|---|
| 16 |  | 180° | C, 62.36; H, 4.10 (C, 62.16; H, 4.23)[5] |

[1] Biochapin A[3].
[2] J. Med. Chem., 1967, 10, 154.
[3] J. Chem. Soc., 1953, 1852.
[4] Calculated for ¼ H$_2$O.
[5] Calculated for ½ H$_2$O.
[6] Trifluoroacetate salt.

EXAMPLE 3

The following 3-substituted-4-oxo-4H-benzopyrans were prepared from the appropriate di-hydroxy-phenyl ketone by the same procedure as described in Example 1. Table 2 shows the structures of compounds prepared together with their melting points and analytical data. The compounds were shown to be single component by T.L.C. and the structures were confirmed by NMR and IR spectroscopy.

TABLE II

| Example | R[1] | R[2] | R[3] | R[4] | m.p. °C | Analysis % (Theoretical in brackets) |
|---|---|---|---|---|---|---|
| 17 | cyclohexyl | H | OH | H | 202° | C, 73.55; H, 6.7 (C, 73.75; H, 6.6) |
| 18 | cyclopentyl | H | H | OH | 203° | C, 73.2; H, 6.0 (C, 73.0; H, 6.1) |
| 19 | cyclopentyl | H | OH | H | 219° | C, 73.1; H, 5.9 (C, 73.0; H, 6.1) |
| 20 | cyclohexyl | H | Cl | OH | 252° | C, 63.6; H, 5.45 (C, 63.6; H, 5.5) |
| 21 | phenyl | H | H | OH | 208° (lit.[1] 213°) | |
| 22 | 4-methoxyphenyl | H | H | OH | 258–259° (lit.[2] 257–258°) | |
| 23 | 1-naphthyl | H | H | OH | 305° | C, 78.7; H, 4.2 (C, 79.1; H, 4.2) |
| 24 | 2-naphthyl | H | H | OH | 278° | C, 79.2; H, 4.3 (C, 79.1; H, 4.2) |
| 25 | 4-methoxyphenyl | CH$_3$ | H | CH$_3$ | 150–151° | C, 76.5; H, 5.7 (C, 77.1; H, 5.75) |

TABLE II-continued

|  |  |  |  |  |  |  |
|---|---|---|---|---|---|---|
| Example | R¹ | R² | R³ | R⁴ | m.p. °C | Analysis % (Theoretical in brackets) |
| 26 | 4-hydroxyphenyl | OH | H | CH₃ | 188–190° | C, 71.55; H, 4.5 (C, 71.6; H, 4.5) |
| 27 | 4-hydroxyphenyl | CH₃ | H | OH | >320° | C, 70.1; H, 4.5 (C, 70.5; H, 4.6)[3] |
| 28 | 3-chlorophenyl | OH | H | CH₃ | 148–149° | C, 65.7; H, 3.9 (C, 66.0; H, 4.0)[3] |
| 29 | 4-hydroxybenzyl | OH | H | CH₃ | 228° | C, 72.1; H, 5.2 (C, 72.3; H, 5.0) |
| 30 | 3-chlorophenyl | OCH₃ | H | OCH₃ | 135–136° | C, 64.3; H, 4.1 (C, 64.6; H, 4.1) |

[1] J. Chem. Soc., 1934, 1121.
[2] J. Endocrin., 1962, 24, 341.
[3] Calculated for ¼ H₂O.

EXAMPLE 4

2,4,6-Trihydroxy-phenyl 4-fluoro-benzyl-ketone (1.31 g, 5 mmole) was dissolved in dimethylacetamide (5.0 ml) and borontrifluoride etherate (2.1 g, 15 mmole) was added cautiously. This solution was then added to a solution of methane-sulphonyl chloride (1.71 g, 15 mmole) in dimethylacetamide (5 ml) and the resulting mixture was heated on the steam batch for 75 minutes. The reaction mixture was poured into cold water (75 ml) and the crystalline diacetate was collected by filtration. The product was hydrolysed by heating in 50% methanolic hydrochloric acid (20 ml, 5N) at reflux for 1 hour, the solution was poured into excess cold water and the crystalline precipitate was collected and dried to give 5,7-dihydroxy-3-p-fluoro-phenyl-2-methyl-4-oxo-4H-benzopyran, m.p. 222°–223°. NMR of the diacetate confirmed that cyclisation had taken place. The product was identical on T.L.C. with a sample prepared via the standard Allen-Robinson synthesis.

I claim:

1. A method of promoting growth or improving feed conversion efficiency in animals which comprises the oral administration to said animals of feed containing per ton 1 to 100 grams of 7-Hydroxy-3-(naphth-2-yl)-4-oxo-4H-benzopyran.

* * * * *